United States Patent [19]
Glidden

[11] Patent Number: 5,855,561
[45] Date of Patent: Jan. 5, 1999

[54] BACK SUPPORT WITH FREEDOM OF ROTARY MOTION

[76] Inventor: Shawn Glidden, 150 Ligon St, #1001, Clemson, S.C. 29631

[21] Appl. No.: 932,804

[22] Filed: Sep. 15, 1997

[51] Int. Cl.$^6$ ...................................................... A61F 5/00
[52] U.S. Cl. .................................................. 602/19; 2/92
[58] Field of Search .............................. 602/19; 128/846, 128/870; 2/2, 92

[56] References Cited

U.S. PATENT DOCUMENTS

| | | | |
|---|---|---|---|
| 1,316,915 | 9/1919 | Meyer et al. | 602/19 |
| 1,650,650 | 11/1927 | Pieper | 602/19 |
| 5,140,995 | 8/1992 | Uhl . | |
| 5,400,801 | 3/1995 | Archer, III . | |
| 5,503,621 | 4/1996 | Miller | 602/19 |
| 5,685,831 | 11/1997 | Floyd | 602/19 |

*Primary Examiner*—Linda C. M. Dvorak
*Attorney, Agent, or Firm*—David H. Jaffer

[57] ABSTRACT

A back support for preventing injury to the spinal column that allows a user a limited amount of freedom of rotary motion. The apparatus includes an upper support, which in use extends from a top end approximately at the neck of a user to a bottom end at the thoracic lumbar transition region. At this point, the bottom end of the upper support is connected by way of a limited motion rotary flex joint to a top end of a lower support, which in use extends from the thoracic lumbar transition region to the tail bone or sacrum region. Both the upper and lower supports are contoured to conform with the shape of the spine and surrounding bodily structure to distribute any impact forces, and except for the length and contour, the upper and lower supports are of similar construction. A preferred embodiment of the supports includes a rigid core member extending the length of each support. The bottom end in the core of the top support and top end of the core in the bottom support are connected together through the flex joint. The rotary motion is provided by the flex joint through use of a ball enclosed in a cage. Four pins are anchored in the ball and protrude through holes in the cage. They are then anchored in the core of the upper support. This allows freedom of rotary motion of the ball in the cage, and therefore the upper support relative to the lower support, within the limits set by interference of the pins in the corresponding cage holes.

6 Claims, 3 Drawing Sheets

CROSS SECTION A-A

CROSS SECTION A-A

CROSS SECTION B-B

BACK SUPPORT WITH FREEDOM OF ROTARY MOTION

BACKGROUND OF THE INVENTION

1. Field of the Invention

The present invention relates generally to apparatus for protecting the spinal column, and more particularly to a back support constructed as two pieces interconnected by a rotary flex joint.

2. Background of the Invention

The design and use of protective back supports has been the subject of attention in the past. Some sporting activities require the use of a back support, a typical example being motorcycle racing. U.S. Pat. No. 5,140,995 by Uhl discloses a device for protecting the spinal column. It includes a flat, elastic, deformable body 12, for direct contact with a user's back, upon which are riveted a series of plate elements having a raised bridge shaped center portion providing clearance for the spinal column. The effect of the raised portion is to direct the force of an impact to the areas on each side of the spinal column. The multiplicity of plate elements also allows some conformance to the shape of a user's back. A similar design is disclosed in U.S. Pat. No. 5,400,801 by Archer, III. Both of these prior art devices use a single, flat deformable body as a base material, upon which is mounted a series of plates, contoured to avoid contact with the spine in the event of an impact. In both cases, the force of an impact to a plate is directed to the area of body structure directly beneath, and to a limited extent the area surrounding the plate receiving the impact. This transfer of force to such a limited area is a disadvantage of the use of a multiplicity of plates in that an injury is less likely when the force of impact is as widely distributed as possible. Another disadvantage is that the normal side to side rotary motions of a user are nearly impossible, and forward/backward motion is very restricted.

It is therefore apparent that a back support is needed that distributes the force of an impact over as broad an area as possible, and simultaneously allows freedom of motion.

SUMMARY OF THE INVENTION

It is therefore an object of the present invention to provide an improved back support for preventing injury to the spinal column and surrounding bodily structure.

It is a further object of the present invention to provide an improved back support that protects the spinal column from injury while allowing a limited degree of rotary motion.

Briefly, a preferred embodiment of the present invention includes a back support for preventing injury to the spinal column that allows a user a limited amount of freedom of rotary motion. The apparatus includes an upper support, which in use extends from a top end approximately at the neck of a user to a bottom end at the thoracic lumbar transition region. At this point, the bottom end of the upper support is connected by way of a limited motion rotary flex joint to a top end of a lower support, which in use extends from the thoracic lumbar transition region to the tail bone or sacrum region. Both the upper and lower supports are contoured to conform with the shape of the spine and surrounding bodily structure to distribute any impact forces, and except for the length and contour, the upper and lower supports are of similar construction. A preferred embodiment of the supports includes a rigid core member extending the length of each support. The bottom end in the core of the top support and top end of the core in the bottom support are connected together through the flex joint. The rotary motion is provided by the flex joint through use of a ball enclosed in a cage. Four pins are anchored in the ball and protrude through holes in the cage. They are then anchored in the core of the upper support. This allows freedom of rotary motion of the ball in the cage, and therefore the upper support relative to the lower support, within the limits set by interference of the pins in the corresponding cage holes.

IN THE DRAWING

DESCRIPTION OF THE PREFERRED EMBODIMENT

Figure 1A:
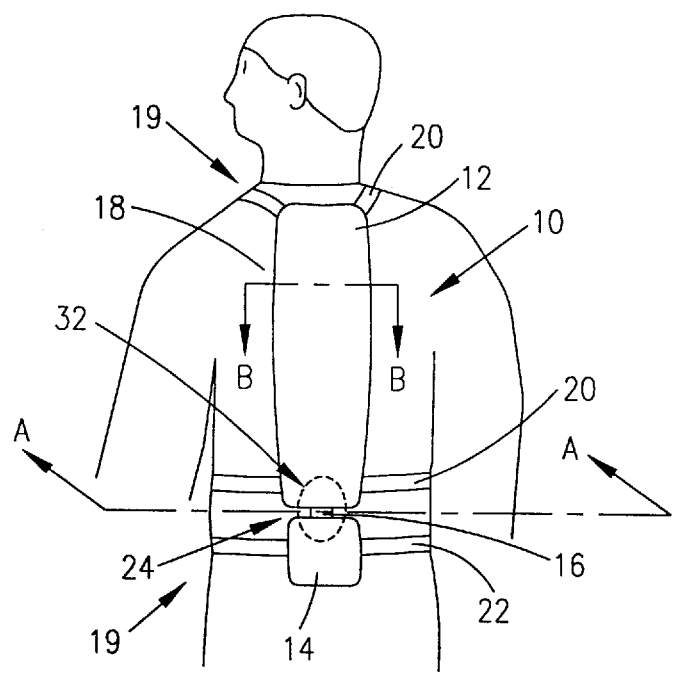
FIG. 1A illustrates the back support of the present invention installed on a user.

Referring now to FIG. 1A of the drawing, a preferred embodiment of the back support 10 of the present invention includes an upper support 12 and lower support 14 joined together by flex joint 16. The back support 10 is mounted to a user with a harness 19, including a first harness portion 20 used to secure the upper portion 12 to the back 18 of a user, and a second harness portion 22, preferably in the form of a strap to retain the lower support 14 in position. The upper and lower supports 12 and 14 distribute the force of an impact to the back over a larger area.

The incorporation of the flex joint allows the user a great deal of freedom of movement, while retaining the protection of a single piece back support. The flex joint 16 is positioned over the thoracic lumbar transition region of the spine 24 which has by far the most flexibility, and is designed to permit rotary motion within safe limits, the design details of which will be fully described in the following descriptions. Although the joint 16 allows rotary motion, it is constructed to provide a secure connection between the upper and lower supports which disallows lateral motion between the upper and lower supports.

Figure 1B:
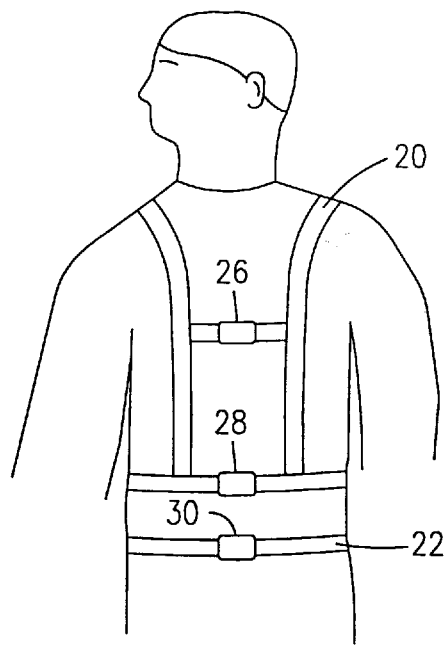
FIG. 1B is a frontal view of a user, illustrating the harness for retaining the back support.

FIG. 1B shows a frontal view of a preferred embodiment of the harness 20 and strap 22, including buckles 26, 28 and 30.

Figure 2:
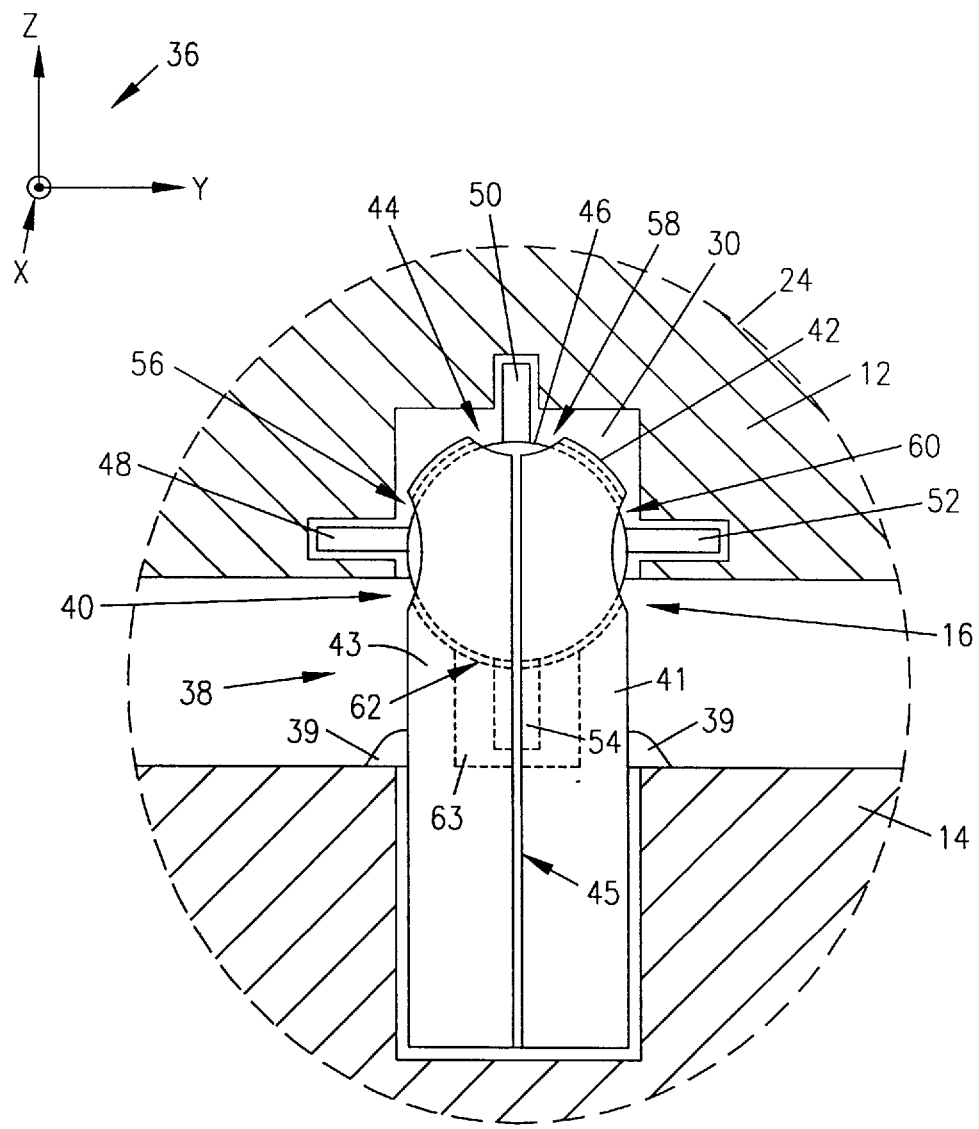
FIG. 2 is an enlargened, cross-sectional view showing the flex joint construction details.

FIG. 2 is a cross-section A—A of area 32 of FIG. 1A indicated by the dashed line. The figure shows the details of construction of the flex joint 16. The coordinates for reference in the following discussion pertaining to FIG. 2 are indicated in diagram 36.

The flex joint 16 includes a post 38 securely embedded in the material of the lower support 14. The post 38 extends out from the lower support 14 towards the upper support 12, the protruding end 40 having a cage 42 formed therein. The preferred construction as shown in FIG. 2 for the post 38 is constructed in two halves 41 and 43, the post divided down the length on axis, as indicated at 45. The interior 44 of the cage 42 is spherical for rotatably retaining a ball 46. Four pins 48, 50, 52 and 54, extend from the ball 46 through corresponding openings 56, 58, 60 and 62 in the cage 42.

The method of attaching the post 38 to the lower portion 14 can be any of the various ways known to those skilled in the art. FIG. 2 shows weld joints 39, but the post could also be soldered, or a very tight press fit, etc. Other alternative structures will be apparent to those skilled in the art. For example, the portion 41 of the post could be a riser with a flange mounted on the lower portion. Such variations are included in the spirit of the present invention.

As shown, the four pins lie in the Y–Z plane, with pins 48 and 52 lying on the Y axis, and pins 50 and 54 on the Z axis. The protruding ends of pins 48, 50 and 52 are embedded in the material of the upper support 12. This structure allows rotary motion of the upper and lower supports relative to each other, giving the user significant freedom of motion while at the same time providing protection. The amount of rotary motion possible is determined by the size and shape of the openings 56–62 in the cage 42. Opening 62 is actually entrance to a bore 63 in the pin 38 at the bottom of the cage as shown. These openings can be of any shape, such as circular, elliptic, etc. as required for the desired range of motion for a particular user. The limit of motion occurs when rotation of the ball brings a pin in contact with the side of a corresponding hole.

Defining the Z axis coincident with pins 50 and 54, as the ball 46 rotates around the Z axis, one or both of pins 48 and 52 eventually come in contact with the edges of their corresponding holes 56, 60 which stops the rotation. Similarly, as the ball rotates on the Y axis, defined by the axis of pins 48 and 52, one or more of the pins 50 and 54 will come in contact with an edge of their corresponding holes 58, 62, and motion will be restricted. As the ball rotates around the X axis, which points out of the drawing as shown and is perpendicular to the plane of the pins, one or more of the pins will eventually come into contact with the edge of a corresponding hole and motion will stop.

The above described construction of the rotary joint is given by way of example. Other methods of constructing a rotary joint that allows limited motion will be apparent to those skilled in the art, and these are included in the spirit of the present invention.

Figure 3:
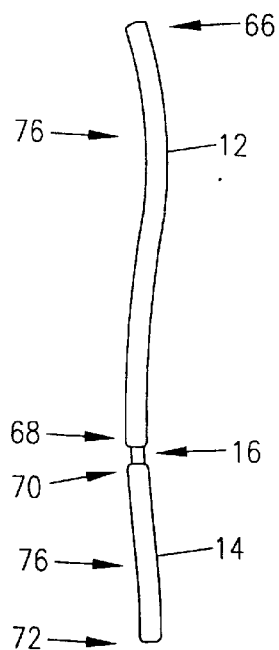
FIG. 3 illustrates the contour of the back support for conformance to the spine.

The back support 10 is formed to match the anatomical shape of the wearer, both above and below the flex joint. A side view illustrating a typical shape is shown in FIG. 3. The harness is omitted for clarity of illustration. The lower support 14 is contoured to follow the body shape from the tail bone or sacrum region upward to the flex joint 16, which is located in the region of the thoracic lumbar transition.

The upper and lower supports 12 and 14 are constructed from lightweight but strong materials. A preferred construction is illustrated in the cross-sectional view B–B (referenced to FIG. 1) shown in FIG. 4A. A strong, lightweight one piece core material 64 is used for each of the two supports 12, 14. In the upper support, it extends from near the top 66 (FIG. 3) to the bottom 68 where it provides a strong material for installation of the pins 48–52 of FIG. 2. Using this preferred construction method, the portions of the supports 12 and 14 shown in FIG. 2 are actually core material 64. In the lower support, core material 64 extends from the top 70 of the lower support to near the bottom 72. A preferred core 64 material is titanium, but other materials such as aluminum alloys can also be used. The core material 64 is surrounded by an encasing material 74, preferably constructed from a material such as carbon fiber. The underside 76 of the supports 12, 14 is designed to distribute the energy of an impact. A preferred embodiment includes a foam covering 78, mounted to the support body with adhesive 80 and provides comfort and aids in distribution of impact energy.

The foam 78 can be selected from a variety of densities and material types. For example, a lesser density, thicker foam can be used to distribute the forces, or a higher density material can be precontoured to the user's back. This is illustrated in FIG. 4B, as an example of a contoured support portion 82 in the upper back area to conform with the curvature of the ribs and spine.

Figure 4A:
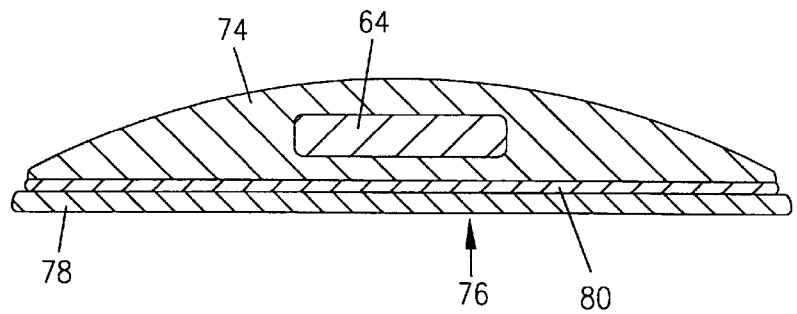
FIG. 4A shows a cross-section for illustrating the structure of the upper and lower supports.
Figure 4B:
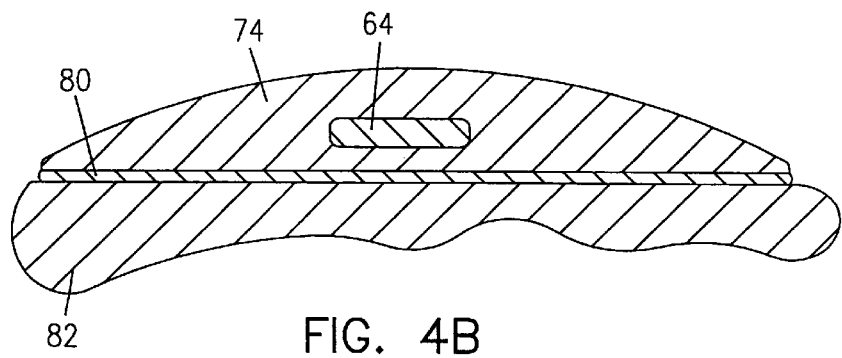
FIG. 4B is a cross sectional view of a back support with a contoured surface.

Although a three piece construction of the supports 12, 14 is shown in FIGS. 4A and 4B, other construction methods are included in the spirit of the invention. For example, the core 64 and encasing 74 combination could be a single piece of material having sufficient strength, and could be used alone, without the use of the material 78, if contoured to distribute the forces. For example, the overall structure of FIG. 4B could be a single, unified material.

Although a preferred embodiment of the present invention has been described above, it will be appreciated that certain alterations and modifications thereof will be apparent to those skilled in the art. It is therefore intended that the appended claims be interpreted as covering all such alterations and modifications as fall within the true spirit and scope of the invention.

What is claimed is:

1. A back support comprising:
   (a) an upper support;
   (b) a lower support;
   (c) a flex joint for connecting said upper support to said lower support, said flex joint allowing limited freedom of rotational motion of said upper support relative to said lower support, wherein said flex joint includes:
      (i) a ball with a first plurality of pins extending therefrom, and a second plurality of said first plurality of said pins anchored in said upper support;
      (ii) a cage in which said ball resides, said cage having a wall with holes for passage of said pins; and
      (iii) means for securing said cage to said lower support whereby said upper support can rotate within limits, relative to said lower support, said limits dependent on the size and shape of said holes and said pins.

2. A back support as recited in claim 1 wherein
   (a) said upper support has a rigid one piece core; and
   (b) said lower support has a rigid one piece core.

3. A back support as recited in claim 2 wherein
   (a) said one piece core of said upper support is encased in an encasing material; and
   (b) said one piece core of lower support is encased in an encasing material.

4. A back support as recited in claim 3 further comprising:
   (a) upper support foam means attached to said upper support for distributing an impact force evenly over a user's body; and
   (b) lower support foam means attached to said lower support for distributing an impact force evenly over a user's body.

5. A back support as recited in claim 2 wherein said upper support and said lower support are configured to conform to the shape of a user's spine.

6. A back support as recited in claim 1 further comprising:
   (a) first harness means for securing said upper support to the body of a user; and
   (b) second harness means for securing said lower support to the body of a user.

* * * * *